Figure 1:
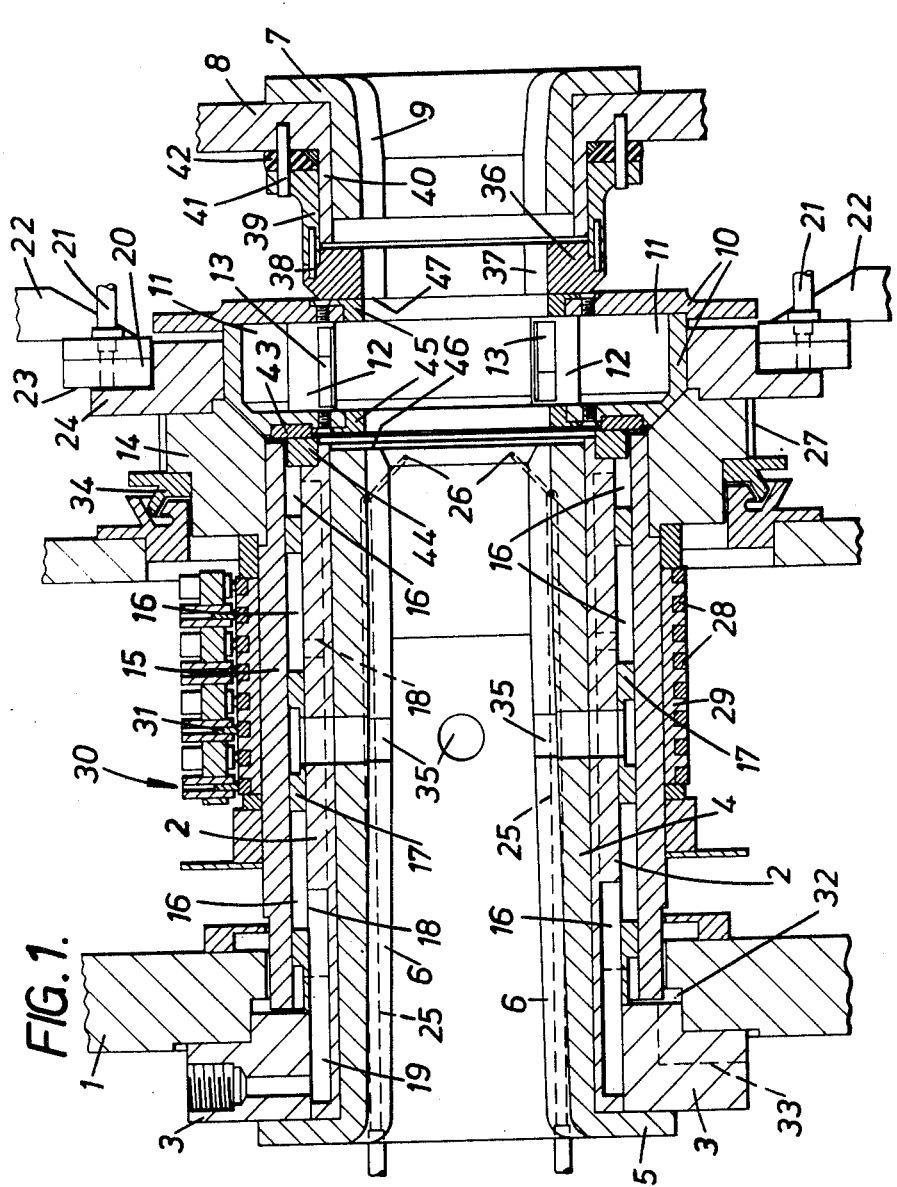

United States Patent [19]

Lewis

[11] 4,084,444
[45] Apr. 18, 1978

[54] ROTARY ULTRASONIC TESTING APPARATUS

[75] Inventor: Richard Lewis, Rushden, England

[73] Assignee: British Steel Corporation, London, England

[21] Appl. No.: 685,158

[22] Filed: May 11, 1976

[30] Foreign Application Priority Data

May 13, 1975 United Kingdom ............... 20149/75

[51] Int. Cl.² ............................................. G01N 29/04
[52] U.S. Cl. .................................................... 73/622
[58] Field of Search .......... 73/67.5 R, 67.8 R, 67.8 S, 73/67.9, 71.5 US

[56] References Cited

U.S. PATENT DOCUMENTS

| | | | |
|---|---|---|---|
| 3,415,111 | 12/1968 | Chattaway et al. ............... | 73/67.8 S |
| 3,533,281 | 10/1970 | Hetherington ................. | 73/71.5 US |
| 3,791,201 | 2/1974 | Dory ................... | 73/67.8 S |
| 3,848,461 | 11/1974 | Hetherington et al. ........... | 73/67.8 S |
| 3,854,326 | 12/1974 | Hetherington et al. ........... | 73/67.8 S |

*Primary Examiner*—Richard C. Queisser
*Assistant Examiner*—Stephen A. Kreitman
*Attorney, Agent, or Firm*—Bacon & Thomas

[57] ABSTRACT

Rotary ultrasonic testing apparatus comprises an annular stator; a replaceable annular ultrasonic probe assembly mounted for rotation on the stator; and first and second fixed replaceable annular guideways for the articles to be tested, said guideways having internal configurations arranged to conform to the cross-section of the article to be tested and provide a close tolerance guide therefor, and said guideways each having a side surface adjacent the probe assembly which serves at least partially as a radially inwardly extending side wall of the probe assembly.

6 Claims, 2 Drawing Figures

ROTARY ULTRASONIC TESTING APPARATUS

This invention relates to rotary ultrasonic testing apparatus of the kind used to test elongate articles of uniform cross-section, such as steel tubes or bars for example, for flaws and dimensional accuracy by rotating an ultrasonic probe assembly in a close pitched helix about the articles, whilst acoustically coupling the probe assembly to the articles by means of a liquid such as water.

It is an object of the present invention to provide rotary ultrasonic testing apparatus of this kind with the facility for accommodating quickly and simply such articles of differing external diameters and of non-circular cross-section for testing.

According to the invention there is provided rotary ultrasonic testing apparatus comprising an annular stator; a replaceable annular ultrasonic probe assembly mounted for rotation on the stator; and first and second fixed replaceable annular guideways for the articles to be tested, said guideways having internal configurations arranged to conform to the cross-section of the article to be tested and provide a close tolerance guide therefor, and said guideways each having a side surface adjacent the probe assembly which serves at least partially as a radially inwardly extending side wall of the probe assembly.

It is to be seen that by means of the invention it is possible to provide a testing arrangement for non-circular cross-section articles by ensuring simply that the annular probe assembly has sufficient clearance to rotate about the article, whilst the use of side surfaces of the close tolerance guideways as side walls of the probe assembly ensures that coupling liquid supplied to the probe assembly for acoustic coupling purposes does not excessively leak away.

The apparatus can be used for testing circular cross-section articles, in which case (as also with non-circular articles) the apparatus has the advantage that articles of different sizes can be accommodated without requiring the probe assembly to be replaced.

The probe assembly may comprise an open channel, the opening of the channel being directed radially inwards. In this case the aforesaid side surfaces of the guideways serve as extensions of the inwardly extending side walls of the probe assembly.

The probe assembly may itself be replaceable and/or it may include replaceable inserts to extend the range of article sizes it can accommodate.

In one form of the invention, the first fixed annular guideway is carried by the stator, the probe is disposed beyond one end of the stator, and the second fixed annular guideway is mounted separate from the stator on the opposite side of the probe assembly from the stator.

The second guideway may comprise a member resiliently urged into bearing contact with one side of the probe assembly, and may comprise a sleeve fitting within an annular mounting, replaceable by sliding from the mounting.

The first guideway may likewise comprise a sleeve fitting within the stator and replaceable by sliding away from the stator at the end opposite to the probe assembly.

The ultrasonic probe assembly may be secured to one end of a sleeve mounted for rotation upon the stator.

Figure 2:
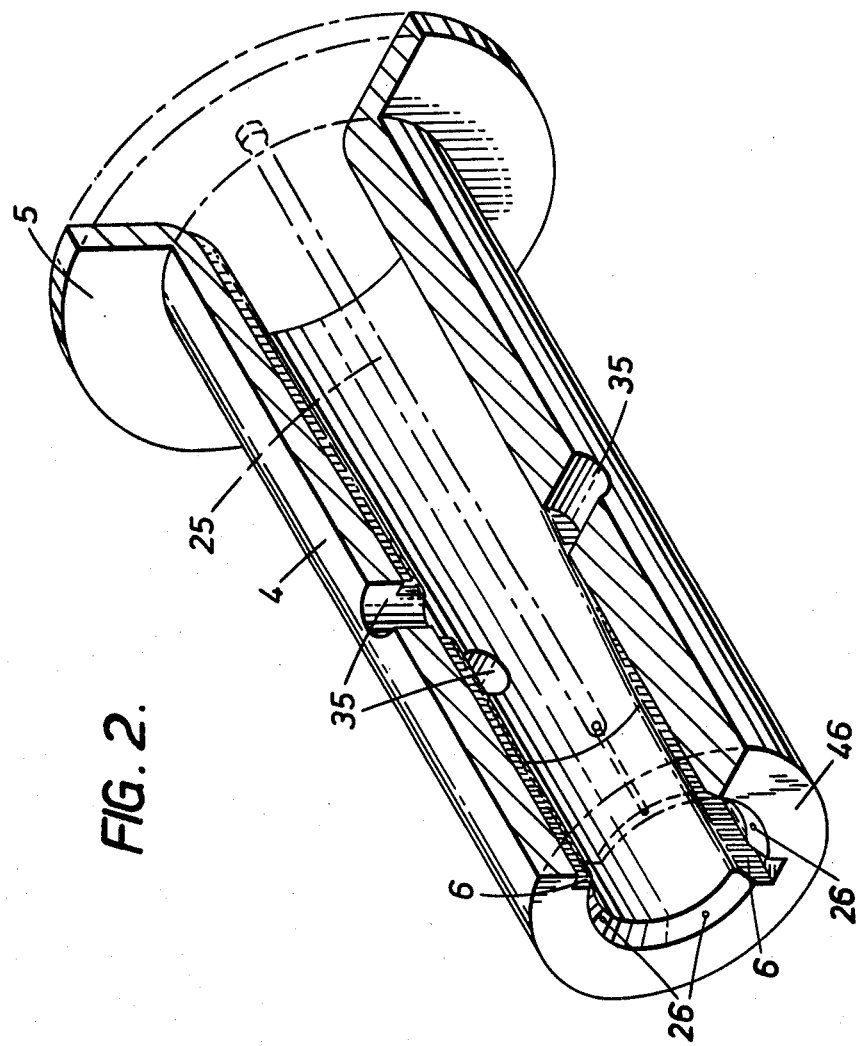

In order that the invention may be more fully understood, one embodiment thereof will now be described by way of example with reference to the accompanying drawings in which:

FIG. 1 is a sectional elevation of rotary ultrasonic testing apparatus for testing steel tubes provided with diametrically opposed external longitudinal fins; and FIG. 2 is an isometric view of a tube guideway of the apparatus of FIG. 1.

The rotary test apparatus illustrated is suitable, for example, for testing steel tubes of outside diameter between ½ inches and 2½ inches and consists essentially of two main units: a stationary unit and a rotating unit. The stationary unit comprises a stainless steel support member 1 carrying a stator in the form of a bronze stub axle 2 having an annular flange 3. A fixed but removable stainless steel sleeve 4 fits within the stub axle 2 and has a flange 5 at one end abutting against the flange 3 of the axle 2. The sleeve 4 is of increasing wall thickness part way along its length such that its internal diameter tapers away from the flanges 5. Diametrically opposed longitudinal grooves 6 are provided along its inner walls whereby the sleeve 4 is capable of acting as a first close tolerance guideway for longitudinally finned tubes to be tested as they are passed through the apparatus. A fixed but removable flanged sleeve 7 is mounted on a support 8 separate from but aligned with the sleeve 4. The flanged sleeve 7 is provided with diametrically opposed longitudinal grooves 9 corresponding to grooves 6 in sleeve 4 and acts as a second close tolerance guideway for the tube to be tested in combination with other parts to be described more fully hereinbelow.

The rotating unit of the apparatus includes a rotatable probe assembly ring 10 disposed coaxially between the sleeves 4 and 7.

The ring 10 is provided with an annular channel shaped chamber 11 within which are mounted for ultrasonic probe transducers 12 (two only of which is shown). These transducers comprise epoxy resin stud like members having shafts of circular cross-section, and a transducing crystal element 13 is mounted on the shaft of each transducer.

Each of the transducers 12 is mounted in the probe assembly for rotation about the longitudinal axis of the transducer, a mechanism (not shown) being provided for adjusting the rotational position of each transducer so that the transducer can be very accurately aligned and adjusted for the particular direction of ultrasonic wave transmission and reception required.

The probe assembly 10 is secured to an annular support ring 14. The ring 14 is, in turn, secured to an annular rotor sleeve 15 fitting around the stub axle 2 for rotation thereabout. A hydrostatic journal bearing is provided between the sleeve 15 and the axle 2, this bearing being provided by recesses 16 provided in a bearing sleeve 17 fitting tightly around the outer surface of the axle 2. Each recess 16 is connected by means of inlet orifices 18 to a water supply channel 19 in the flange 3.

In addition to the provision of a hydrostatic journal bearing for a rotating unit, the apparatus incorporates a hydrostatic thrust bearing arrangement to prevent axial movement of the rotating unit, the arrangement including a bearing ring 20 and water supply channels 21.

The bearing ring 20 is secured to a fixed support 22 such that its bearing face 23 abuts against a radially outwards extension 24 of the probe assembly 10.

In use, the ultrasonic transducers 12 are coupled to the tube to be tested via water, and to this end the annular chamber 11 is arranged to be filled and kept filled with water by means of four water channels 25 extending along the first guideway sleeve 4 and connecting to water inlet orifices 26 opening inwardly of a chamfered portion of the guideway closely adjacent to the assembly 10. We have found that in practice such an arrangement is capable of filling, and maintaining filled, the annular chamber 11 with water when in use.

The rotor sleeve 15 is provided with a toothed flange 27 which in use is engaged by a driving belt (not shown) for rotation of the sleeve.

The rotor sleeve 15 carries an integral slip ring unit comprising eight slip rings 28 moulded into an annular block 29 of electrically insulating material. Each transducer 12 is connected to a separate pair of the rings 28 via electrical leads (not shown). A brush assembly 30 carries brushes 31 connecting to the rings 28 whereby the probes are connected to an external power source and monitoring unit.

It is necessary to ensure that in use no water from the liquid bearings or from the ultrasonic coupling arrangement leaks to the slip rings and brushes, and to this end water exhausting from the journal bearing at the flanged end is prevented from entering the slip ring area by means of a water trap 32 provided with an escape orifice 33.

At the other end of the journal bearing, the slip ring assembly is protected from the ingress of water by means of a thrower ring assembly 34 mounted on the ring 14.

To eliminate liquid pressure build-up due to leakage from the hydrostatic bearings, escape openings 35 extend through the wall of the stub axle 2 to the interior of the sleeve 4.

The second tube guideway, in addition to sleeve 7, includes an annular member 36 having diametrically opposed internal grooves 37 corresponding to grooves 9 in sleeve 7. The member 36 is secured by means of pins 38 to an outer-sleeve 39 slidable on a tubular portion 40 of the fixed support 8 and attached thereto by means of dowels 41. Interposed between the support 8 and the outer-sleeve 39 is a ring 42 of elastomeric material which urges the member 36 towards the probe assembly 10.

Engagement between the assembly 10 and the stub axle 2 is protected by respective bearing surfaces 43 and 44.

The radially innermost parts of the walls of the probe assembly 10 are provided by means of annular inserts 45 screwed to the assembly 10, and the member 37 of the second guideway bears against one of these surfaces.

For the operation of the apparatus, water is supplied to the various hydrostatic bearings so that the probe assembly can be rotated. Water is then supplied to the orifices 26 so that the annular chamber 11 fills the water (by centrifugal action) to the radially inner limits of inserts 45 at the most. It will be observed that this is of greater diameter than the fins of the tubes to be tested. A longitudinally finned tube can now be fed into guideway sleeve 4 and through the apparatus. As it passes through the probe assembly, its close tolerance fit within the first and second guides enables water within the chamber 11 completely to surround the tube for full acoustic coupling therewith within a very short time (about 2 to 5 seconds in practice). Thus in operation, surfaces 46 and 47 of the first and second guideways serve as radially inward extensions of the chamber 11.

If tubes of a different size or external configuration are to be tested, the apparatus can readily be adapted by replacing the sleeve 4, sleeve 7 and member 36, and either inserts 45 or the whole of probe assembly 10 by appropriately shaped and dimensioned new parts.

I claim:

1. In a rotary ultrasonic testing apparatus comprising an annular stator; a replaceable annular ultrasonic probe assembly mounted for rotation on the stator; first and second fixed replaceable annular guideways for the articles to be tested located one on each side of the probe assembly, said guideways having internal configurations arranged to conform to the cross-section of the article to be tested and provide a close tolerance guide therefor, the improvement wherein the internal dimension of said guideways adjacent said probe assembly is smaller than the internal dimension of said probe assembly and said guideways each have an end surface adjacent the probe assembly which serve as radially inwardly extending side walls immediately adjacent the opposite sides of the probe assembly.

2. Apparatus as claimed in claim 1 wherein the probe assembly comprises radially inwardly, spaced apart, side walls forming therebetween an open channel, the opening of the channel being directed radially inwards.

3. Apparatus as claimed in claim 2 wherein the probe assembly includes replaceable annular inserts for attachment to the side walls thereof to extend the range of article sizes that can be accommodated by the apparatus.

4. In a rotary ultrasonic testing apparatus comprising an annular stator; a replaceable annular ultrasonic probe assembly mounted for rotation on but disposed beyond one end of the stator; a first fixed replaceable annular guideway for the articles to be tested carried by the stator; and a second fixed replaceable annular guideway mounted separate from the stator on the opposite side of the probe assembly from the stator, said guideways having internal configurations arranged to conform to the cross-section of the article to be tested and provide a close tolerance guide therefor, the improvement wherein the internal dimension of said guideways adjacent said probe assembly is smaller than the internal dimension of said probe assembly and said guideways each having a side surface adjacent the probe assembly which serves at least partially as a radially inwardly extending side wall of the probe assembly.

5. Apparatus as claimed in claim 4 wherein the second guideway comprises a sleeve fitting within an annular mounting replaceable by sliding from the mounting.

6. Apparatus as claimed in claim 4 wherein the second guideway comprises a member resiliently urged into bearing contact with one side of the probe assembly.

* * * * *